United States Patent

Skuster

[11] 4,442,038
[45] Apr. 10, 1984

[54] CONVERTING ENZYME INHIBITORS

[75] Inventor: James R. Skuster, Norwich, N.Y.

[73] Assignee: Norwich Eaton Pharmaceuticals, Inc.

[21] Appl. No.: 419,152

[22] Filed: Sep. 17, 1982

[51] Int. Cl.³ ............................................. C07C 153/11
[52] U.S. Cl. ................................ 260/455 R; 562/426; 260/501.12
[58] Field of Search ....................... 260/501.12, 455 R; 424/316; 562/426

[56] References Cited

U.S. PATENT DOCUMENTS

| | | | |
|---|---|---|---|
| 4,105,789 | 8/1978 | Ondetti et al. | 260/455 R |
| 4,140,864 | 2/1979 | Ondetti et al. | 260/455 R |
| 4,156,786 | 5/1979 | Ondetti et al. | 260/455 R |
| 4,256,761 | 3/1981 | Suh et al. | 260/501.12 |
| 4,339,600 | 7/1982 | Ondetti et al. | 260/455 R |

Primary Examiner—James H. Reamer
Attorney, Agent, or Firm—Anthony J. Franze

[57] ABSTRACT

N-(4-phenylcyclohexyl)glycines of the formula:

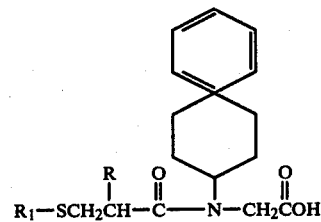

and salts thereof wherein R is H or lower alkyl and $R_1$ is hydrogen or benzoyl are useful as angiotensin I converting enzyme inhibitors.

5 Claims, No Drawings

CONVERTING ENZYME INHIBITORS

This invention is concerned with derivatives of N-(4-phenylcyclohexyl)glycines which have the formula:

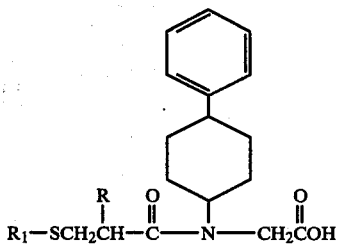

and salts thereof wherein R is H or lower alkyl and $R_1$ is hydrogen or benzoyl.

Manifestly the compounds represented by formula (I) exist in geometric isomeric forms as well as diastereoisomeric forms or racemic mixtures thereof; all being within the scope of this invention.

The compounds are potent inhibitors of the enzyme responsible for converting the decapeptide angiotensin I to the octapeptide angiotensin II. Angiotensin II is the powerful pressor agent implicated as the causative agent in some forms of hypertension.

Of late, it has been recognized that a substance capable of interrupting the pathway whereby angiotensin II is produced, viz., the conversion hereabove referred to, presents a useful and effective means of combatting hypertension associated with that pressor agent.

It has been discovered that the compounds of this invention are possessed of noteworthy activity in inhibiting angiotensin I converting enzyme. Thus, in in vitro techniques designed to evince such activity these compounds are highly effective. For example, they inhibit the pure converting enzyme isolated from rabbit lung tissue at levels from about 0.04 μm to 0.30 μm. They are, therefore, notable angiotensin I converting enzyme inhibitors.

The compounds of this invention are not limited to in vitro manifestations of their converting enzyme inhibiting propensity. Upon oral administration, a dose-dependent antihypertensive effect in acute aortic coarctation hypertensive rats is elicited. Oral dosage of from 1 mg/kg to 200 mg/kg administered as a suspension in 0.5% Methocel solution achieved a reduction of 40–50 mm Hg in mean arterial blood pressure in such rats.

The compounds of this invention can be composed in a variety of dosage forms such as tablets, capsules, solutions and the like for convenient administration employing classical excipients and adjuvants with which there is no incompatibility. Such dosage forms contain from 10 to 500 mg of a compound of formula (I) or a salt thereof in a unit dosage form in accordance with accepted pharmaceutical practice.

In order that this invention may be readily available to and understood by those skilled in the art, the following examples are appended.

EXAMPLE I trans-N-(4-Phenylcyclohexyl)glycine-1,1-dimethylethyl ester Hydrochloride To a stirred solution of 4-phenylcyclohexanone (50.0 g, 0.287 mole) dissolved in methanol (500 ml) was added a solution of glycine-dimethylethyl ester (12.6 g, 0.096 mole) dissolved in methanol (50 ml) while cooling on an ice bath. Molecular sieves (10 g, 3 Å) was added, then a solution of NaCNBH$_3$ (18.0 g, 0.287 mole) dissolved in methanol (50 ml) was added dropwise. Stirring was continued overnight at room temperature. The filtered solution was concentrated under reduced pressure to an oily residue. This oily residue was dissolved in ether (500 ml), washed with NaHCO$_3$, H$_2$O and dried over MgSO$_4$. The filtered solution was treated with saturated ether/HCl (20 ml, ~5 N ether/HCl). The precipitated solid was collected and air dried to give 14.5 g. Recrystallization from acetonitrile and air drying gave 12.2 g. Melting point, dec. <250°.

Anal. Calcd. for $C_{18}H_{27}NO_2 \cdot HCl$: C, 66.34; H, 8.66; N, 4.30 Found: C, 66.32; H, 8.70; N, 4.20

EXAMPLE II (A)

trans-N-(3-benzoylthio-1-oxopropyl)-N-(4-phenylcyclohexyl)glycine-1,1-dimethylethyl ester To a mixture of the compound of Example I (0.60 g, 0.0018 mole) and CH$_2$Cl$_2$ (6 ml) was added N-methylmorpholine (0.44 g, 0.0043 mole). The resulting mixture was cooled on an ice bath and 3-benzoylthiopropanoyl chloride (0.45 g, 0.0020 mole) was added dropwise. After stirring 10 min the mixture was filtered removing the insolubles. The CH$_2$Cl$_2$ solution was washed with 20% citric acid, H$_2$O, 10% NaHCO$_3$, H$_2$O and dried over MgSO$_4$. The filtered solution was concentrated under reduced pressure to dryness and then azeotroped with diethyl ether to a semi-solid residue. This residue was dissolved in a small amount of diethyl ether and precipitated with hexane to give a crystalline solid. Drying in vacuo at 60° overnight gave 0.48 g (0.001 mole, 55%) of trans-N-(3-benzoylthio-1-oxopropyl)-N-(4-phenylcyclohexyl)glycine-1,1-dimethylethyl ester.

(B)

trans-(3-Benzoylthio-1-oxopropyl)-N-(4-phenylcyclohexyl)glycine

A solution of trans-N-(3-benzoylthio-1-oxopropyl)-N-(4-phenylcyclohexyl)glycine-1,1-dimethylethyl ester (0.48 g, 0.001 moles) and saturated acetic acid/NCl (10 ml, saturated at 0°) was stirred at room temperature for 30 min. The solution was concentrated under reduced pressure to an oily residue. This residue was chromatographed on a column (1.5×30 cm) of LH-20 Sephadex eluting with methanol. The fractions containing product were collected and concentrated under reduced pressure to dryness. Hexane was added and the suspension concentrated under reduced pressure to a solid. Drying in vacuo at room temperature gave 200 mg (0.0005 mole 50%) of title compound; melting point 125°–128°.

Anal. Calcd. for $C_{24}H_{27}NO_4S$: C, 67.74; H, 6.40; N, 3.29 Found: C, 67.71; H, 6.56; N, 3.21

EXAMPLE III (A)

trans-(S)-N-(3-Benzoylthio-2-methyl-1-oxopropyl)-N-(4-phenylcyclohexyl)glycine-1,1-dimethylethyl ester A solution of the compound of Example I (1.2 g, 0.0037 mole) was dissolved in CH$_2$Cl$_2$ (20 ml), washed with saturated NaHCO$_3$ (3×20 ml), H$_2$O (2×20 ml) and dried over MgSO$_4$. The filtered solution was taken to a total volume of 25 ml with CH$_2$Cl$_2$. This solution was cooled on an ice bath (15°-20°), triethylamine (0.45 g, 0.0044 mole) was added and then (S)-benzoyl-β-mercaptoisobutyric acid chloride [(1.07 g, 0.0044 mole dissolved in $CH_2Cl_2$ (2 ml)] was added dropwise over 2-3 min. The solution was stirred under ambient conditions for 4.0 hours. The resulting solution was washed with saturated $NaHCO_3$ (4×30 ml), $H_2O$ (2×50 ml), 20% citric acid (4×30 ml), $H_2O$ (2×50 ml) and dried over $MgSO_4$. The filtered solution was concentrated under reduced pressure to give 1.66 g (0.0033 mole), 89%) of trans-(S)-N-(3-benzoylthio-2-methyl-1-oxopropyl)-N-(4-phenylcyclohexyl)glycine-1,1-dimethylethyl ester as an oil.

(B)
trans-(S)-(—)-N-(3-Benzoylthio-2-methyl-1-oxopropyl)-N-(4-phenylcyclohexyl)glycine A solution of trans-(S)-N-(3-benzoylthio-2-methyl-1-oxopropyl)-N-(4-phenylcyclohexyl)glycine-1,1-dimethylethyl ester (1.60 g, 0.0032 mole) and saturated acetic acid/NCl (20 ml, saturated at 0°) was stirred at room temperature for 1.0 hour. The resulting solution was concentrated under reduced pressure to a semi-solid residue. Trituration with anhydrous ether and air drying gave 1.09 g of a solid. Recrystallization from isopropanol, air drying and drying in vacuo at 60° gave 0.90 g (0.0020 mole), 62.5%) of title compound; melting point 180°-181°$[\alpha]_D^{20} = -40.6$ (C=0.5, MeOH).

Anal. Calcd. for $C_{25}H_{29}NO_4S$: C, 68.31; H, 6.65; N, 3.19 Found: C, 68.32; H, 6.58; N, 3.11

EXAMPLE IV (A)
cis-N-(4-Phenylcyclohexyl)glycine-1,1-dimethylethyl ester Hydrochloride To a stirred solution of 4-phenylcyclohexanone (34.26 g, 0.20 mole, Ald.) dissolved in methanol (200 ml) with warming was added dropwise a solution of glycine-1,1-dimethylethyl ester [(9.17 g, 0.07 mole) dissolved in methanol (50 ml)]. To this solution was added molecular sieves (5 g, 3 Å). This mixture was heated to reflux and reflux maintained for 6.0 hours. To the mixture was added more molecular sieve (2 g, 3 Å) and 5% Pd/C dry. This mixture (still warm) was subjected to hydrogenation overnight on a Parr apparatus. The filtered solution was concentrated under reduced pressure to dryness. Hexane (800 ml) was added and a solid was collected. This solid was dissolved in ether and washed with saturated $NaHCO_3$, $H_2O$ and dried over $MgSO_4$. The filtered solution was acidified with saturated HCl/ether. The precipitated solid was collected and air dried to give 8.0 g (0.025 mole) of the cis isomer.

(B)
cis-(S)-N-(3-Benzoylthio-2-methyl-1-oxopropyl)-N-(4-phenylcyclohexyl)glycine-1,1-dimethylethyl ester A solution of cis-N-(4-phenylcyclohexyl)glycine-1,1-dimethylethyl ester hydrochloride [(3.26 g, 0.01 mole) in $CH_2Cl_2$ (75 ml)] was washed with saturated $NaHCO_3$, $H_2O$, dried over $MgSO_4$ and filtered. To this stirred solution was added triethylamine (1.11 g, 0.011 mole) and then (S)-3-benzoyl-β-mercaptoisobutyric acid chloride (2.67 g, 0.011 mole) was added dropwise. Stirring was continued for 1.5 hours at room temperature. The solution was washed with 20% citric acid, $H_2O$, saturated $NaHCO_3$, $H_2O$ and dried over $MgSO_4$. The filtered solution was concentrated under reduced pressure to an oily residue (4.8 g). This crude oil was chromatographed on Waters "Prep 500" on normal phase silica eluting with ethyl acetate/hexane (12.5/87.5) giving 4.1 g of an oil.

(C)
cis-(S)-(—)-N-(3-Benzoylthio-2-methyl-1-oxopropyl)-N-(4-phenylcyclohexyl)glycine dicyclohexylamine salt A solution of cis-(S)-N-(3-benzoylthio-2-methyl-1-oxopropyl)-N-(4-phenylcyclohexyl)glycine-1,1-dimethylethyl ester (4.1 g, 0.0085 mole) and saturated acetic acid/HCl (25 ml, saturated at 0°) was stirred at room temperature for 1.5 hours. The solution was concentrated under reduced pressure to an oily residue. This residue was dissolved in $CH_2Cl_2$, washed with $H_2O$ (2×) and dried over $MgSO_4$. The filtered solution was concentrated under reduced pressure to an oily residue. The oily residue was dissolved in ether and dicyclohexylamine was added. After standing several days the solid was collected and air dried. Recrystallization from acetonitrile and air drying gave 3.1 g (0.005 mole, 59%) of title compound. The analytical sample was prepared by drying a small portion in vacuo at room temperature. Melting point 135°-137° $[\alpha]_D^{20} = -17.3°$ (C=0.5, MeOH).

Anal. Calcd. for $C_{25}H_{29}NO_4S \cdot C_{12}H_{23}N$: C, 71.57; H, 8.44; N, 4.51 Found: C, 71.93; H, 8.04; N, 4.41

EXAMPLE V

N-(3Mercapto-1-oxopropyl)-N-(trans-4-phenylcyclohexyl)glycine

Under a layer of nitrogen a mixture of the compound of Example II (B) (1.0 g, 0.0023 ml) and 10 ml $H_2O$ was stirred and cooled in an ice bath. Ammonium hydroxide (10 ml, conc.) was added and the solution was stirred at room temperature for 18 hr. A precipitate formed and was removed by filtration. The filtrate was extracted with chloroform (7×50 ml). The aqueous layer was then cooled and acidified to pH=1 with conc. HCl. The product precipitated and was collected. It was further purified by silica gel chromatography using $CHCl_3$/MeOH (18:1) as eluent. Desired fractions from the column were combined and concentrated to an oil which, upon treatment with ether, crystallized yielding 0.069 g (9.3%) of product, m.p. 125°-130°.

What is claimed is:

1. A compound of the formula:

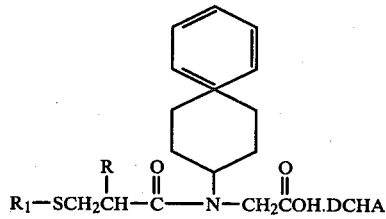

wherein R is H or lower alkyl and DCHA is dicyclohexylamine or nil and $R_1$ is hydrogen or benzoyl.

2. The compound trans-(3-benzoylthio-1-oxopropyl)-N-(4-phenylcyclohexyl)glycine.

3. The compound trans-(S)-(—)-N-(3-benzoylthio-2-methyl-1-oxopropyl)-N-(4-phenylcyclohexyl)glycine.

4. The compound cis-(S)-N-(3-benzoylthio-2-methyl-1-oxopropyl)-N-(4-phenylcyclohexyl)glycine dicyclohexylamine salt.

5. The compound N-(3-mercapto-1-oxopropyl)-N-(trans-4-phenylcyclohexyl)glycine.

* * * * *